United States Patent [19]

Carlson

[11] 4,321,577
[45] Mar. 23, 1982

[54] INTEGRAL HUMIDITY SENSOR/HEATER CONFIGURATIONS

[75] Inventor: Richard O. Carlson, Scotia, N.Y.

[73] Assignee: General Electric Company, Schenectady, N.Y.

[21] Appl. No.: 124,133

[22] Filed: Feb. 25, 1980

[51] Int. Cl.³ .............................................. H01L 7/00
[52] U.S. Cl. .................................. 338/35; 252/520; 252/521; 338/309; 422/98
[58] Field of Search ................... 338/35, 34, 308, 309; 73/336.5, 73; 340/602; 29/610; 252/518, 520, 521; 324/61 R; 422/98; 23/232 E; 427/126

[56] References Cited

U.S. PATENT DOCUMENTS

| | | | |
|---|---|---|---|
| 2,806,991 | 9/1957 | White | 338/34 X |
| 3,479,257 | 11/1969 | Shaver | 338/34 X |
| 3,839,616 | 10/1974 | Risman | 338/34 X |
| 3,926,858 | 12/1975 | Ichinose et al. | 252/518 X |
| 3,961,301 | 6/1976 | Fraioli | 338/35 |
| 4,015,230 | 3/1977 | Nitta et al. | 338/35 |
| 4,080,564 | 3/1978 | Nitta et al. | 338/35 X |
| 4,086,556 | 4/1978 | Nitta et al. | 338/35 |
| 4,110,260 | 8/1978 | Yamamoto et al. | 252/520 X |

OTHER PUBLICATIONS

Birox Resistor Compositions 9318 and 9319, Electronic Materials 5/76.
R. C. Evans, *An Introduction to Crystal Chemistry*, Cambridge University Press, Second Edition, 1964—p. 173.

*Primary Examiner*—C. L. Albritton
*Attorney, Agent, or Firm*—Charles E. Bruzga; James C. Davis, Jr.; Marvin Snyder

[57] ABSTRACT

A humidity sensitive device is formed of a humidity sensitive material comprised of a magnesium aluminate spinel and titania material. The humidity sensitive device includes various means for applying heat to the humidity sensitive material to purge the humidity sensitive material of foreign substances and also thereby to restore or rejuvenate the characteristics of the humidity sensitive material.

10 Claims, 9 Drawing Figures

INTEGRAL HUMIDITY SENSOR/HEATER CONFIGURATIONS

BACKGROUND OF THE INVENTION

This invention relates to humidity sensitive devices and more particularly to a humidity sensitive device comprised of a magnesium aluminate spinel and a titania material.

Humidity sensitive devices are used in various applications to measure the humidity of atmospheric environments. The measured humidity may be used to control the operation of a process being performed. An example of a humidity controlled process is the microwave cooking of a food substance in which the heating cycle is dependent on the measured humidity within the microwave oven. Such a humidity controlled microwave oven is described, for example, in U.S. Pat. No. 4,080,564 issued to T. Nitta et al., Mar. 21, 1978. Also described in U.S. Pat. No. 4,080,564 is the use of radiant heat to periodically purge the humidity sensor of foreign substances, such as oil, that may be deposited on the sensor during the microwave heating of the food substance. The foreign substance may interfere with the humidity sensing characteristics of the device.

It is also known that humidity sensitive devices may be used in air conditioning apparatus and also heating apparatus. The air conditioner apparatus may sense the humidity as an indication to determine when moisture should be removed from the environment in order to provide a more pleasantly cooled environment. Conversely, a heating apparatus may sense the humidity as an indication to determine when moisture should be added to the environment in order to provide a more pleasantly warmed environment.

In the above-given applications of humidity sensitive devices it is desirable that the humidity sensor provide an accurate measurement of the humidity. Also, it is desirable that the humidity sensitive devices provide repeatability, that is, the same measurement of humidity be provided under similar conditions over a periodic time.

Repeatability is hindered when the characteristics of the humidity sensitive material, such as a metal oxide, change or drift over a period of time. The material characteristics of the metal oxides may be restored or rejuvenated by the application of heat to elevate the material to a relatively high temperature in the order of 400° C. If a humidity sensitive material requires frequent rejuvenation to maintain repeatability, the required rejuvenation may interfere with the desired heating or cooling process being performed.

Accordingly, an object of the present invention is to provide a humidity sensitive device that provides an accurate measurement of the humidity and requires relatively infrequent rejuvenation.

A further object of the present invention is to provide a humidity sensitive device having various means for applying heat for rejuvenation.

A still further object of the present invention is to provide a low cost, endurable and accurate device that may be used in various atmospheric environments, such as, microwave ovens, air conditioners, and heating apparatus to measure humidity.

These and other objects of this invention will become apparent upon consideration of the following detailed description taken together with the accompanying drawings.

BRIEF SUMMARY OF THE INVENTION

The present invention is directed to a humidity sensitive device having heating means to purge the device of foreign substances and also thereby to restore the humidity sensitive impedance characteristic of the device.

In accordance with one preferred embodiment of the invention a device for sensing ambient humidity comprises a fired layer of a composition of magnesium aluminate spinel and titania, means adjoining the fired layer for applying heat to the fired layer, at least one conductor connected to the fired layer and at least second and third conductors connected to the means for applying heat.

The features of the invention believed to be novel are set forth with particularity in the appended claims. The invention, itself, however, both as to its organization and operation, together with further objects and advantages thereof, may best be understood by reference to the following description taken in conjunction with the accompanying drawings.

DESCRIPTION OF THE PREFERRED EMBODIMENT

Figure 1:
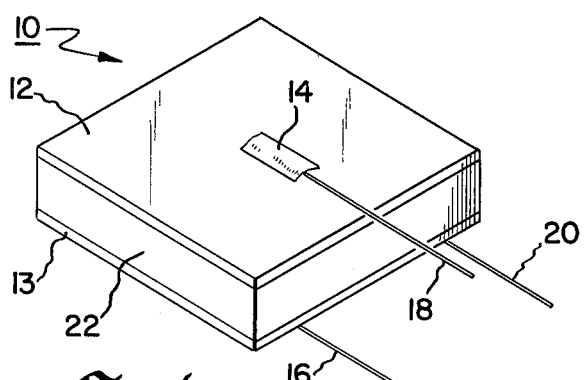
FIGS. 1 and 2 are perspective views showing a top and a bottom surface, respectively, of a humidity sensitive device according to one embodiment of the present invention.

Referring to FIG. 1, there is shown a perspective view of a top portion of a humidity sensitive device 10 according to one embodiment of this invention. The humidity sensitive device 10 is comprised of a fired layer 22 of humidity sensitive material, coatings 12 and 13 formed of a resistive material placed on the top and the bottom surfaces, respectively, of the fired layer 22, and three conductors 16, 18 and 20 which are typically formed of metallic wire such as platinum wire.

The fired layer 22 of humidity sensitive material is formed of an aluminum spinel oxide with an additive of a titania material. The composition of the humidity sensitive material is formed of magnesium aluminate with a preferred range of 70 to 90 mol percent and of titania with a preferred range of 10 to 30 mol percent. The compounds of the humidity sensitive material, in the aforementioned proportions, are intimately mixed with water. The mixed solution is pressed into typical dimensions of 1.0 cm (400 mils) by 1.0 cm (400 mils) by 0.5 mm (20 mils) and then fired at a relatively high temperature in the order of 1300° C.

The resistive material comprising layers 12 and 13 is typically formed from a BIROX material. BIROX is a trademark of E. I. duPont de Nemours and Company for a group of their thick film resistor compositions. The type material may be selected, such as du Pont composition 9318, from the Thick Film Catalog dated May 1976 of E. I. duPont de Nemours and Company (Inc.), Wilmington, Del., 19898, which is herein incorporated by reference. The BIROX material comprising layers 12 and 13 is typically prearranged in a paste type form and then spread onto the top and bottom surfaces of layer 22 to form layers 12 and 13, respectively. The coatings 12 and 13 are then fired at a relatively high temperature in the order of 850° C. The fired layers 12 and 13 of the BIROX material have a resistivity on the order of 1.5 to 3.0 ohms per square.

Figure 2:
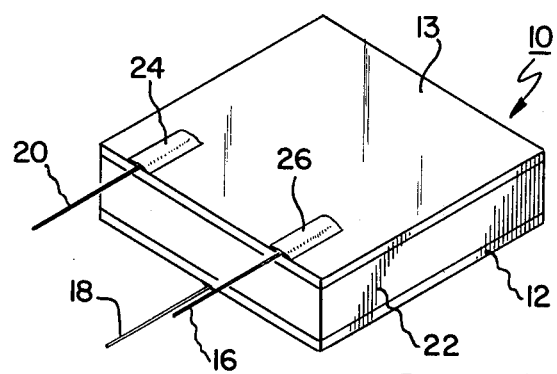

The conductors 16, 18 and 20 are arranged with conductor 18 being placed in a central portion on the BIROX coating 12 and conductors 16 and 20, shown most clearly in FIG. 2, being arranged on the BIROX coating 13 near respective opposite edges thereof. When the conductors 18, 16 and 20 have been arranged on their respective coatings 12 and 13, BIROX coatings 14, 24, and 26, respectively, are applied onto the conductors. The coatings 14, 24 and 26 are then fired to a relatively high temperature in the order of 850° C. Upon the completion of the firing of coatings 14, 24 and 26, the humidity sensitive device 10 has been formed.

Figure 3:
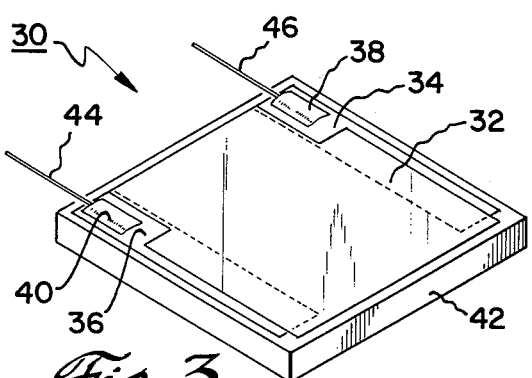
FIGS. 3 and 4 are perspective views showing a top and a bottom surface, respectively, of another embodiment of humidity sensitive device of the present invention.
Figure 4:
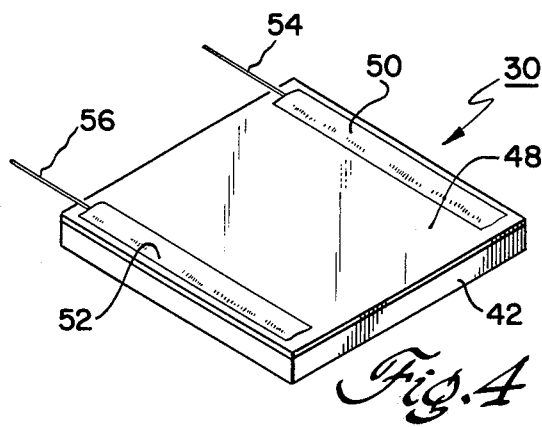

Referring to FIGS. 3 and 4, there are shown perspective views of a top and a bottom surface, respectively, of a humidity sensitive device 30 in accordance with another embodiment of the present invention. Device 30 is similar to device 10 in that its humidity sensitive material, formed in a thick film layer 32, is comprised of magnesium aluminate with a titania additive. The composition of the humidity sensitive material of device 30 is preferably formed, as previously described for device 10, of magnesium aluminate with a preferred range of 70 to 90 mol percent and of titania with a preferred range of 10 to 30 mol percent.

Electrodes 34 and 36, shown in FIG. 3, are formed of a conductor composition, such as E. I. duPont de Nemours & Co. platinum composition 7919, and are attached to an insulating plate 42, by firing at a high temperature designated by the resistor vendor. Electrodes 34 and 36, do not extend over the whole plate 42 but only to the extent shown in phantom and are isolated from each other. The thick film 32 is applied to insulating plate 42 over electrodes 34 and 36 by forming a thick paste of magnesium aluminate with the titania additive and then spreading the paste type composition across a major portion of the top surface of the insulating plate 42. The paste type material is transversely spread onto insulating plate 42 such that the top surface of insulating plate 42 is substantially covered; however, this paste is transversely spread such that most of each electrode 34 and 36 is contacted with the paste type material as shown in FIG. 3. The paste type material is then fired at a relatively high temperature in the order of 1300° C. to form layer 32. Completion of the firing of layer 32 results in layer 32 being affixed to the top surface of insulating plate 42 and also bonded to electrodes 34 and 36.

Figure 5:
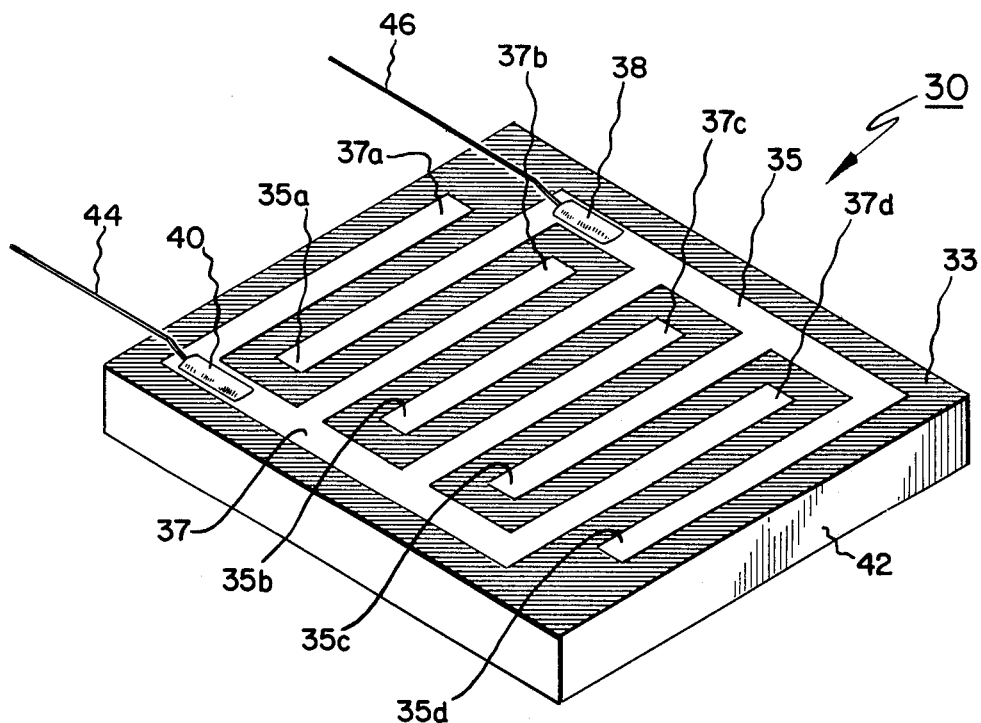
FIG. 5 is a perspective view of a top surface of a humidity sensitive device having interdigitated electrodes affixed thereto.

Referring to FIG. 5, there is shown an alternate embodiment of a pair of electrodes 35 and 37 fabricated in an interdigitated configuration. Electrodes 35 and 37 are formed of the same platinum thick film conductor composition of electrodes 34 and 36. Electrode 35 has a plurality of finger like extensions 35a, 35b, 35c and 35d. Similarly, electrode 37 has a plurality of finger-like extensions 37a, 37b, 37c and 37d. Electrodes 35 and 37 are arranged with respect to each other as shown in FIG. 5, so that the finger-like extensions of each electrode 35 and 37 form a complementary non-contacting configuration in which substantially all of the top surface of the insulating plate 42 is overlayed. The top surface of the insulating plate 42 and electrodes 35 and 37 are covered with a thick paste of the preferred composition of magnesium aluminate and titania additive as layer 33 which serves the same function as layer 32 in FIG. 3. The top surface is fired at a relatively high temperature in the order of 1300° C.

The bottom surface of device 30, shown in FIG. 4, is prepared by first mixing a resistor material, such as BIROX, into a paste type form, and then spreading the paste type material upon the full width of the bottom surface of the insulating plate 42. The BIROX paste is fired at a relatively high temperature in the order of 850° C., to form a coating 48.

Conductors 44 and 46 are positioned, as shown in FIG. 3, onto electrodes 34 and 36, respectively, or as shown in FIG. 5 onto the interdigitated electrodes 35 and 37 respectively. Conductors 54 and 56, shown in FIG. 4, are positioned onto fired layer 48 near the side edges thereof. Conductors 44, 46, 54 and 56 are typically formed of a metallic wire such as platinum wire. A coating of BIROX paste is then placed over each conductor 44, 46, 54 and 56. The BIROX paste is then fired at a relatively high temperature in the order of 850° C., to form fired coatings 38, 40, 50, 52 for conductors 46, 44, 54 and 56, respectively. Completion of the firing for the coatings 38, 40, 50 and 52, completes formation of humidity sensitive device 30.

Figure 6:
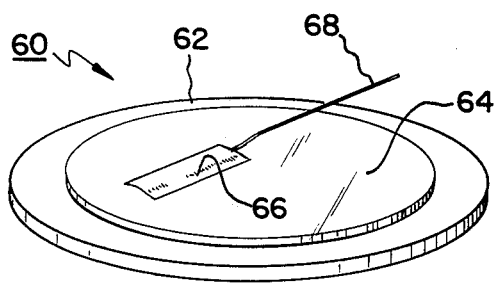
FIGS. 6 and 7 are perspective views showing opposite sides, respectively, of a still further embodiment of the present invention.
Figure 7:
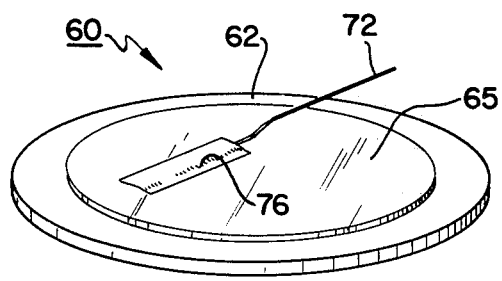

Referring to FIGS. 6 and 7, there are shown, perspective views of respective opposite sides of a humidity sensitive device 60 in accordance with still another embodiment of the present invention. Device 60 is similar to the previously described devices 10 and 30 in that it has a humidity sensitive material 62 preferably formed of the previously described magnesium aluminate with the titania additive, each material having the previously described desired proportions.

The humidity sensitive material 62 having the desired mixed proportions of magnesium aluminate and titania is conventionally formed into a disk shaped by pressing and then the disk shaped material 62 is fired at a relatively high temperature in the order of 1300° C. The disk shaped material 62 has a typical diameter of 1.5 cm (0.6 inches) and a typical thickness of 0.5 mm (20 mils).

The central portion of each side of the humidity sensitive material 62 is then coated with a thick paste of resistive and heat absorbing material, such as BIROX. The paste type material is then fired at a relatively high temperature in the order of 850° C., to form layer 64, shown in FIG. 6, and layer 65 shown in FIG. 7.

Conductors 68 and 72, each typically formed of a platinum wire material are positioned onto layers 64 and 65, respectively. An additional coating of BIROX paste is next applied to each conductor 68 and 72 and then fired to a relatively high temperature in the order of 850° C., to form fired coatings 66 and 70 respectively. Completion of fired coatings 66 and 70, completes formation of device 60.

Figure 8:
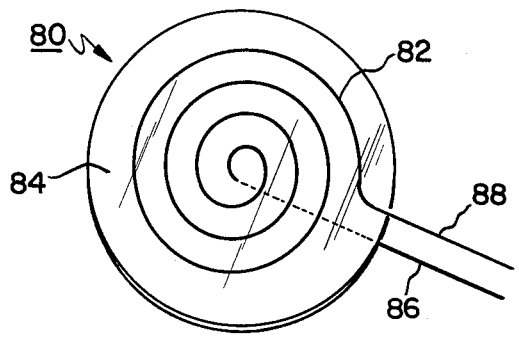
FIG. 8 illustrates a heating device used in conjunction with the device shown in FIGS. 6 and 7.

Referring now to FIG. 8, there is shown a disk shaped heating means 80 that is used in conjunction with humidity sensitive device 60. Heater means 80 is comprised of resistors 86 and 88 each typically formed of a nichrome wire material, and a insulating sheet 84 formed of a mica material. Resistors 86 and 88 are arranged to form a spiral type configuration 82. Insulating sheet 84 is positioned with respect to the configuration 82 such that the spiral configuration 82 is positioned in the central portion of the insulating sheet 84. Insulating sheet 84 has a typical thickness of 0.25 mm (10 mils) and a diameter of 1.77 cm (0.7 inches).

All of the described devices 10, 30 and 60, each having a humidity sensitive material formed of magnesium aluminate and titania additive, have an impedance (Z) characteristic related to the relative humidity (H), in percent, sensed by devices 10, 30 and 60 in accordance with the following relationship:

$$Z = A \times \epsilon^{(-BH)} \quad (1)$$

where

A is a constant having a typical value of $4.6 \cdot 10^7$ for configuration 60 and B is a constant having a typical value of 0.077

It has been empirically determined that over a period of time, such as 24 hours, the impedance characteristic of the composition of magnesium aluminate and titania additive changes or shifts slightly due to small changes in the B constant and also it is believed due to small changes in the A constant. It has been further empirically determined that the original impedance characteristic of the composition of magnesium aluminate and the titania additive may be recovered or rejuvenated by a process of heating the composition of magnesium aluminate and titania additive to a relatively high temperature in the order of 400° C. for a relatively short period of time in the order of 2 minutes. After the composition of magnesium aluminate with the added titania has been rejuvenated, it provides subsequent accurate measurements of relative humidity over a time period in the order of 24 hours.

It has been still further empirically determined that other known humidity sensitive materials such as a chromite sensor formed of a magnesium chromite and a titania additive require more frequent rejuvenation periods as compared to the typical 24 hour periodic rejuvenation required by the composition of magnesium aluminate and titanium sensors. It should now be noted that by decreasing the frequency of rejuvenation periods a corresponding increase in usage of the humidity sensitive device to measure humidity during a controlled process, such as microwave cooking, results. It should be appreciated that this invention provides humidity sensors 10, 30, and 60 allowing relatively long periods between rejuvenation and thus providing relatively long periods in which the devices 10, 30 or 60 may be used to accurately measure relative humidity as a means for controlling a heating or cooling process.

Although a heating or cooling apparatus controlled by a humidity sensor, such as devices 10, 30 and 60, is not considered a part of this present invention, typical heating and cooling processors will now be discussed in order to describe the interconnections and interaction of devices 10, 30 or 60 with a typical cooling or heating apparatus. Furthermore, for the following description it is to be assumed that the discussed heating or cooling apparatus is controlled by an electrical device, such as a microprocessor, so that the devices 10, 30 or 60 supplying an electrical signal indicative of humidity may be utilized to their fullest advantages.

Reference is now made to FIG. 1 to describe the desired interconnections and interaction of device 10 into a typical heating or cooling apparatus. As previously discussed, the impedance of device 10 varies in a direct relationship to the relative humidity sensed by device 10 in accordance with equation (1). The impedance value of device 10 may be measured by a conventional capacitance-conductance bridge device set at 1000 Hz and connected to conductors 18 and 16 or connected to conductors 18 and 20. The measured impedance value of device 10 is indicative of the relative humidity of the environment in which device 10 is situated.

During microwave cooking of food substances the foods emit a humid vapor which may be used for controlling a heating process for the food substances. The amount of humid vapor emitted by the food substances determines the relative humidity within the environment of the microwave oven. Device 10 may be used as a means for sensing the relative humidity within the microwave oven and thus provide the microwave apparatus with the means for controlling the cooking of the food substances.

Also, when food substances are heated they emit oily substances, that may be deposited on the humidity sensing device to thereby interfere with measurement accuracy of the device. Device 10 includes the means to purge itself of the oily substances and while doing so also restore the humidity measuring accuracy of its humidity sensitive material. The purging of the foreign substance from device 10 and the concomitant rejuvenation of the device may be accomplished by applying a dc or ac signal, in the order of a few volts, to conductors 16 and 20. Conductors 16 and 20, as previously discussed, are bonded to the resistive layer 13 formed of fired BIROX. The fired layer 13 having a resistivity in the order of 1.5 to 3.0 ohms per square, will heat up to a relatively high temperature in the order of 400° C. Elevating the layer 13 to 400° C., will correspondingly elevate the device to substantially the same temperature and thus drive off foreign substances from the device 10. Also, elevating layer 13 to 400° C. raises the temperature of the fired layer 22 to a temperature in the order of 400° C., which will correspondingly restore the humidity measuring accuracy of the composition of the magnesium aluminate with the titania additive. It should be noted that the rendered rejuvenation of device 10 provides for an accurate subsequent measurement of relative humidity during a relatively long time period in the order of 24 hours.

Thus, it should now be appreciated that device 10 having the advantage of providing an accurate measurement of relative humidity for a relatively long time period and having the advantage of self-purging itself of foreign substances, provides the microwave cooking art with a desirable humidity sensing device. It should also be appreciated that device 10 may be used in other devices such as an air conditioner apparatus in which the device 10 may be used to measure the humidity of the environment in which it is situated. Device 10 may be interrogated by an electrical device, such as a microprocessor, to determine the relative humidity sensed by device 10. The microprocessor may use the information from device 10, in the form of an electrical signal, as a control signal transmitted to a control means to control removal of moisture from the air in order to provide a more pleasantly cooled environment. Similarly, device 10 may also be used by a microprocessor within a heating apparatus to determine if moisture should be added to the air in order to provide a more pleasantly warmed environment.

Device 30 has usages similar to those described for device 10. The means for monitoring the impedance of the humidity sensitive device 30 is provided by conductors 44 and 46 shown in FIG. 3. The means for supplying a dc or ac signal to elevate the temperature of the heat absorbing coating 48 of device 30 and thereby also elevate the temperature of device 30 is provided for by conductors 54 and 56 shown in FIG. 4.

Device 60 constitutes a humidity sensitive device that may have uses similar to those described for device 10. However, the heat received by device 60 to purge itself of foreign substances and also to restore its humidity measuring accuracy is received from heater means 80.

Figure 9:
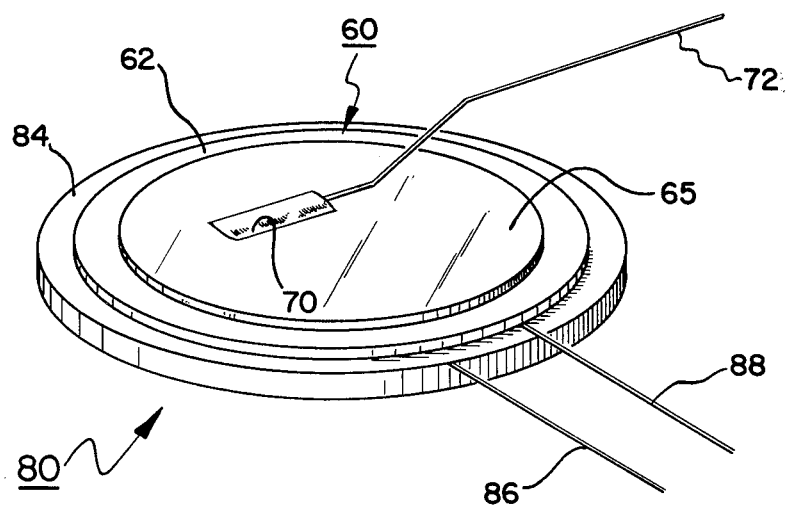
FIG. 9 illustrates the placement of the humidity sensitive device of FIGS. 6 and 7 onto the heating means of FIG. 8.

FIG. 9 illustrates the arrangement of device 60 with respect to heater means 80. Device 60 is arranged in an adjoining position such that it lays upon the central portion of heater means 80. Heating means 80 generates heat upon the application of a dc or ac signal to its nichrome resistors 86 and 88. The generated heat of heater means 80 is transmitted to device 50 via conduction and radiation. The heat absorbing layers 64 and 65 of device 60 absorb heat energy from heater means 80, thereby elevating the temperature of device 60 to its desired value.

It should now be appreciated that this invention provides humidity sensitive devices 10, 30 and 60 having means to purge themselves of foreign materials and only requiring relatively infrequent rejuventation to restore their impedance measuring characteristic thereby also allowing subsequent accurate humidity measurements. The devices are fabricated of metallic components and thus provide a rugged structure for use in various environments.

While the invention has been particularly shown and described with reference to several preferred embodiments thereof, it will be understood by those skilled in the art that various changes in form and detail may be made therein without departing from the true spirit and scope of the invention as defined by the appended claims.

What is claimed is:

1. A device for sensing ambient humidity comprising:
   a fired layer of a composition of magnesium aluminate spinel and titania, said fired layer of said composition comprising a bulk type material with a range of 70 to 90 mol percent of magnesium aluminate and 10 to 30 mol percent of titania;
   means adjoining said fired layer for applying heat to said fired layer;
   at least one conductor connected to said fired layer; and
   at least second and third conductors connected to said means for applying heat.

2. A humidity sensor device according to claim 1 wherein said means for applying heat comprises a first, relatively thin coating of a BIROX resistor material on a first surface of said bulk type material.

3. A humidity sensor device according to claim 2 wherein said one conductor is positioned onto a middle portion of a second surface of said bulk type material having a second coating of BIROX and being bonded to the second surface by said second coating of BIROX, and wherein said second and third conductors are positioned onto opposite edges of the first surface of the bulk type material having the first coating of BIROX, said edge positioned conductor being bonded to the first surface by said first coating of BIROX.

4. A humidity sensor device according to claim 1 wherein said fired layer of magnesium aluminate spinel and titania comprises a paste type composition with a range of 70 to 90 mol percent of magnesium aluminate spinel and 10 to 30 mol percent of titania coated on a first surface of a sheet of alumina insulation material having affixed thereto a pair of interdigitated platinum resistor electrodes.

5. A humidity sensor device according to claim 4 wherein said means for heating comprises a first, relatively thin coating of a BIROX material on a second surface of said alumina insulation material.

6. A humidity sensor device according to claim 5 wherein said one conductor and a fourth conductor are respectively positioned onto said pair of platinum resistor electrodes at opposite edges of said first surface of said alumina insulation material, said one and said fourth conductors each being coated with BIROX material and said second and third conductors being positioned on opposite edges of the second surface of said alumina insulation material, said second and third conductors each being coated with BIROX material.

7. A humidity sensor device according to claim 1 wherein said fired layer of the composition of magnesium aluminate spinel and titania comprises a thin layer of disk type shape with a range of 70 to 90 mol percent of magnesium aluminate and 10 to 30 mol percent of titania.

8. A humidity sensor device according to claim 7 wherein said thin layer of disk type shape further comprises a thin coating of BIROX material on the central portion of opposite sides thereof.

9. A humidity sensor device according to claim 8 wherein said one conductor and a fourth conductor are respectively positioned onto the central portion of opposite surfaces of said BIROX material coating the opposite sides of said thin layer of disk type shape.

10. A humidity sensor device according to claim 9 wherein said means for applying heat to said fired layer is comprised of a pair of nichrome wires arranged in a spiral configuration, and an insulating sheet formed of a mica material, said nichrome wires being positioned in the central portion of insulating sheet and providing a source of heat for transmission directly by radiation and conduction to at least one of said coatings of BIROX material.

* * * * *